United States Patent
Maes et al.

(10) Patent No.: US 8,710,034 B2
(45) Date of Patent: Apr. 29, 2014

(54) METHOD AND COMPOSITION FOR IMPROVING SKIN BARRIER FUNCTION

(75) Inventors: Daniel H. Maes, Huntington, NY (US); Jon Anderson, Boonton, NJ (US); Kenneth D. Marenus, Dix Hills, NY (US); Thomas Mammone, Farmingdale, NY (US); Christina G. Fthenakis, Dix Hills, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 13/441,164

(22) Filed: Apr. 6, 2012

(65) Prior Publication Data

US 2013/0095046 A1    Apr. 18, 2013

Related U.S. Application Data

(63) Continuation of application No. 12/103,806, filed on Apr. 16, 2008, now abandoned, which is a continuation of application No. 09/554,984, filed as application No. PCT/US00/08871 on Apr. 4, 2000, now abandoned.

(51) Int. Cl.
*A01N 45/00* (2006.01)
*A61K 31/59* (2006.01)
*A61K 31/56* (2006.01)

(52) U.S. Cl.
USPC ............................. 514/167; 514/169

(58) Field of Classification Search
None
See application file for complete search history.

(56) References Cited

U.S. PATENT DOCUMENTS

| | | |
|---|---|---|
| 4,760,096 A | 7/1988 | Sakai et al. |
| 4,992,477 A | 2/1991 | Geria |
| 5,084,270 A | 1/1992 | Ciaudelli |
| 5,310,759 A * | 5/1994 | Bockman ............ 514/573 |
| 5,459,165 A | 10/1995 | Bollens et al. |
| 5,508,034 A | 4/1996 | Bernstein |
| 5,529,769 A | 6/1996 | Cho et al. |
| 5,589,178 A * | 12/1996 | Aubert et al. ............ 424/401 |
| 5,589,194 A * | 12/1996 | Tsuei et al. ............ 424/497 |
| 5,658,947 A | 8/1997 | DasGupta et al. |
| 5,679,358 A * | 10/1997 | Bombardelli et al. ....... 424/401 |
| 5,679,656 A | 10/1997 | Hansenne |
| 5,705,145 A | 1/1998 | Miklean et al. |
| 5,726,163 A | 3/1998 | Fujii et al. |
| 5,738,856 A | 4/1998 | Korb et al. |
| 5,747,538 A | 5/1998 | Meybeck et al. |
| 5,834,016 A * | 11/1998 | Naeff et al. ............ 424/450 |
| 5,858,334 A | 1/1999 | Ascione et al. |
| 5,869,711 A | 2/1999 | Philippe et al. |
| 5,882,634 A | 3/1999 | Allard et al. |
| 5,885,565 A | 3/1999 | Elias et al. |
| 5,906,993 A | 5/1999 | Braquet et al. |
| 5,932,234 A | 8/1999 | Simon et al. |
| 5,976,510 A | 11/1999 | Cernasov et al. |
| 5,976,519 A | 11/1999 | Nojiri et al. |
| 5,981,256 A | 11/1999 | Egelrud et al. |
| 6,004,568 A | 12/1999 | Bonte et al. |
| 6,150,381 A | 11/2000 | Subbiah |
| 6,180,119 B1 | 1/2001 | Boussouira et al. |
| 6,183,761 B1 * | 2/2001 | Bissett et al. ............ 424/401 |
| 6,399,048 B1 | 6/2002 | Allard et al. |
| 6,495,147 B1 | 12/2002 | Dumas et al. |
| 6,589,945 B1 | 7/2003 | Wachter et al. |
| 2002/0098207 A1 | 7/2002 | Maes et al. |

FOREIGN PATENT DOCUMENTS

| | | |
|---|---|---|
| CA | 2097997 | 12/1994 |
| CA | 1336762 | 8/1995 |
| DE | 19642872 | 2/1998 |
| DE | 19834812 | 2/2000 |
| EP | 0 386 680 | 9/1990 |
| EP | 0717983 | 6/1996 |
| EP | 0826367 | 3/1998 |
| EP | 0868906 | 10/1998 |
| EP | 0976396 | 2/2000 |
| JP | 60161911 | 8/1985 |
| JP | 05051314 | 2/1993 |
| JP | 05-310526 | 11/1993 |
| JP | 08-208424 | 8/1996 |
| JP | 8-283218 | 10/1996 |
| JP | 09-315931 | 12/1997 |
| JP | 10-500395 | 1/1998 |
| JP | 10-175838 | 6/1998 |
| JP | 10-203992 | 8/1998 |
| JP | 10-511673 | 11/1998 |
| JP | 10-316538 | 12/1998 |

(Continued)

OTHER PUBLICATIONS

PCT International Search Report; International Application No. PCT/US00/08871; Completion Date: Dec. 5, 2000; Date of Mailing: Dec. 12, 2000.

(Continued)

*Primary Examiner* — Alton Pryor
(74) *Attorney, Agent, or Firm* — Julie M. Blackburn

(57) ABSTRACT

The invention relates to a method for improving skin lipid barrier function by applying to the skin a composition comprising effective amounts of a protease inhibitor and a cell differentiation enhancer. The composition is useful in promoting skin lipid barrier repair and maintaining the integrity of the lipid barrier. In this regard, the compositions can be used in the treatment and prevention of dry skin, and associated chrono/proto-aging conditions, in the treatment and prevention of irritation on the skin, in the treatment and prevention of UV-related damage to the skin, and in the enhancement of the retention of self-tanning.

13 Claims, No Drawings

(56) References Cited

FOREIGN PATENT DOCUMENTS

| | | |
|---|---|---|
| JP | 10-330238 | 12/1998 |
| JP | 11005742 | 1/1999 |
| JP | 11-029467 | 2/1999 |
| JP | 11-029468 | 2/1999 |
| JP | 11-171758 | 6/1999 |
| JP | 11-292777 | 10/1999 |
| WO | WO90/01323 | 2/1990 |
| WO | WO94/00127 | 1/1994 |
| WO | WO95/25524 | 9/1995 |
| WO | WO96/20704 | 7/1996 |
| WO | WO98/17244 | 4/1998 |
| WO | WO99/24009 | 5/1999 |
| WO | WO99/62478 | 12/1999 |
| WO | WO99/62481 | 12/1999 |
| WO | WO99/63978 | 12/1999 |
| WO | WO00/45786 | 8/2000 |

OTHER PUBLICATIONS

Pot International Search Report; International Application No. PCT/US00/02750; Completion Date: Apr. 19, 2000; Date of Mailing: Sep. 5, 2000.

Sato, et al.; Cholesterol Sulfate Inhibits Proteases that are Involved in Desquamation of Stratum Corneum; XP-001091104; vol. III; No. 2; The Society for Investigative Dermatology, Inc.; pp. 189-193; Aug. 1998.

Kawasai, et al.; Control System of Desquamation of Stratum Corneum; Fragrance Journal (JP); No. 92; pp. 73-77; 1998. (Relevant passage: p. 76, Lines 10-17 of left column, (Eng. Prtl. Trans.).

Wilden, Wim Van Der, et al.; A skin-identical lipid concentrate for an improved skin-barrier function; Chemical Abstract; Columbus, OH; XP-002135991; Fragrance Journal; vol. 132; 27(10); pp. 71-74; Abstract No. 170820; 1999, (Eng. Abstract).

Abstract 398; Abstracts for the 1996 Annual Meeting Society for Investigative Dermatology, May 1996; The Journal of Investigative Dermatology; vol. 106, No. 4; Apr. 1996.

Abstract 791; Abstracts for the 61st Annual Meeting of the Society for Investigative Dermatology, May 2000; The Journal of Investigative Dermatology; vol. 114, No. 4; Apr. 2000.

Non Final Office Action dated Aug. 14, 2001, for U.S. Appl. No. 09/554,984.

Non Final Office Action dated Jul. 30, 2002, for U.S. Appl. No. 09/554,984.

Non Final Office Action dated Oct. 31, 2003, for U.S. Appl. No. 09/554,984.

Final Office Action dated Aug. 25, 2004, for U.S. Appl. No. 09/554,984.

Non Final Office Action dated Aug. 11, 2006, for U.S. Appl. No. 09/554,984.

Non Final Office Action dated Jan. 29, 2007, for U.S. Appl. No. 09/554,984.

Final Office Action dated Jan. 15, 2008, for U.S. Appl. No. 09/554,984.

Dahmen et al. Boswellic acid, a potent antiinflammatory drug, inhibits rejection to the same extent as high dose steroids. Transplant Proc. 2001. 33(1-2):539-41.

Hisajima et al. Vasodilation produced by forskolin compared with that produced by adenosine in rabbit coronary artery. J. Cardiovasc Pharmacol. 1986. 8(6):1262-7.

D'Orazio et al. Topical drug rescue strategy and skin protection based on the role of McIr in UV-induced tanning. Nature. 2006. 443(7109):340-4.

MedlinePlus U.S. National Library of Medicine, NIH, National Institute of Health, Skin—Abnormally dark or light. URL of this page http://www.nlm.nih.gov/medlineplus/ency/article/003242.htm, reprinted from medline source Feb. 11, 2011.

Dorland's Illustrated Medical Dictionary 897 (29th ed. 2000) W.B. Saunders Company; A Harcourt Health Sciences Company, 2000. p. 897.

Indena product brochure, Esculoside: Vasoactive, anticellulite, microcirculation improver (Dec. 2004).

Indena product brochure, Esculoside: Vasoactive, anticellulite, microcirculation improver (Dec. 2004).

\* cited by examiner

METHOD AND COMPOSITION FOR IMPROVING SKIN BARRIER FUNCTION

This application is a continuation of U.S. Ser. No. 12/103,806 filed Apr. 16, 2008, pending; which is a continuation of U.S. Ser. No. 09/554,984, filed Apr. 4, 2000 now abandoned, which is a national stage filing of International Application US00/08871, filed Apr. 4, 2000, now expired.

FIELD OF THE INVENTION

The invention relates to cosmetic and pharmaceutical compositions. More specifically, the invention relates to topical compositions that are useful in enhancing the function of the skin's natural lipid barrier.

BACKGROUND OF THE INVENTION

Skin is typically characterized as consisting of three distinct layers, namely the stratum corneum, the epidermis and the dermis. The stratum corneum, the outermost layer, is made up of keratinized, cells, surrounded by intercellular space filled with lipids. The stratum corneum provides a substantial physical barrier to penetration of most substances to the lower layers of the skin. In addition to preventing transport of substances to the other skin layers, however, this barrier also aids in prevention of water loss from the skin. Both functions are primarily attributable to the presence of the lipids in the stratum corneum.

There are two sources of the skin surface lipids making up this important barrier; sebaceous glands and the epidermis. The lipids are a diverse group of compounds, comprising triglycerides, diglycerides, ceramides, free fatty acids, wax esters, cholesterol and cholesterol esters, and squalene. The quantity and composition of the skin surface lipids differ from place to place on the body, and may to some extent be related, to the number of sebaceous glands in a given area of the skin. The condition of the skin surface lipids may also be affected by an essential fatty acid deficiency. Additionally, the lipid barrier is easily diminished by exposure to harsh detergents or soaps, it is apparent, then, that the quality of the skin lipid barrier can vary widely, depending on a number of different factors, and therefore, may not always be adequate to perform its protective function optimally.

As an attempt to compensate for what may be a less than adequate lipid barrier, cosmetic compositions frequently incorporate components which compensate for water loss. Examples of such materials are hygroscopic humectants, e.g., urea or propylene glycol, which hold water on the skin; or emollients, e.g., oleyl alcohol or caprylic/capric triglycerides. Certain cosmetic components may be occlusive skin conditioners, which are used to provide an "artificial" barrier; such compounds are frequently lipids which remain on the skin surface, and include various hydrogenated oils, waxes and butters. Although many of these products provide an effective means of steaming water loss from the skin, they do have to be reapplied frequently to maintain the effect, and do not generally constitute a natural-occurring component of the stratum corneum, potentially giving rise to an unnatural, greasy feel to the skin. In addition, various pharmaceutical or cosmetic active agents are also frequently used to treat the symptoms of dry skin-associated conditions; however, in many cases, particularly with pharmaceutical agents, the treatments themselves may cause undesirable side effects in the individual being treated, while ultimately resulting in no actual repair of the lipid barrier.

The most desirable situation, from a functional point of view, is to find a way to enhance the skin's own ability to maintain and/or repair the strength of its barrier, so that the protective barrier formed is completely natural. It has now been discovered that a combination of specific skin active agents results in an unexpected increase in the strength of the natural barrier, by stimulating the production and maintenance of the barrier's naturally occurring components. There is thus provided a new type of cosmetic or pharmaceutical composition which functions by enhancing the skin's own functions, resulting in a more natural means of preventing dry skin and other undesirable results of a deficient lipid, barrier.

SUMMARY OF THE INVENTION

The invention relates to cosmetic and pharmaceutical compositions comprising lipid barrier-enhancing effective amounts of at least one protease inhibitor and at least one cellular differentiation enhancer. The composition can also comprise, in a preferred embodiment, effective amounts of a sterol sulfate, an at least one naturally occurring skin, lipid component. The composition of the invention can be used in a method for strengthening the natural lipid barrier of the skin, as well as other methods of skin treatment that are made possible by the strengthening of the barrier.

DETAILED DESCRIPTION OF THE INVENTION

The combined actives of the composition of the invention have been found to be highly effective in stimulating the repair of a damaged lipid barrier, and therefore, are shown to be useful as well in maintenance of a normal and healthy lipid barrier. For the purposes of the present invention and claims, these abilities will be referred to as strengthening the lipid barrier. The compositions of the invention can strengthen the lipid barrier at least about 40%, relative to a placebo control, as measured by a reduction of transepidermal water loss (TEWL) after a barrier challenge, a standard measurement of barrier function. Preferably, the compositions are capable of reducing TEWL at least about 50%, more preferably at least about 60%, and most preferably at least about 70%. The invention incorporates as essential elements a protease inhibitor and a cellular differentiation enhancer. Protease inhibitors are compounds, usually naturally occurring, which inhibit the action of proteases in the skin. Skin proteases also occur, naturally, and, among other effects, are involved in the breaking down of the collagen and elastin that is required to maintain the healthy appearance of skin, in the present case, the protease inhibitors used in the invention are thought to act by preventing the breakage of the desmosome bond between corneocytes at the skin surface, thereby keeping the outer layer of skin cells intact, in essence delaying desquamation. This skin layer provides a barrier to water loss, and the enhanced retention of the barrier by the delay of desquamation provides reinforces this barrier to the loss of water further. A variety of protease inhibitors are known. Examples of useful protease inhibitors include, but are not limited to, triterpenoid-containing extracts and refined compounds, for example, white birch bark extract, silver birch bark extract, *Boswellia* extract, bearberry extract, *Centella asiatica* extract, or *Pygeum* (*Prunus*) *africanum* extract and individual protease inhibitor compounds that may foe present in these extracts, including betulinol (betulin), foetulinic acid, boswellic acid, ursolic acid, oleanolic acid, oleanol, asiaticoside, asiatic acid, and madagassic acid; phenolic-containing extracts, such as green tea extracts and apple extracts, and compounds contained therein, such as EGCG, EGG, cacechins, phenylpropanoids, and phloretin; protein-based extracts, such as soy protein, or egg protease inhibitors, or cholesterol sulfate and phytosterol sulfates. Preferred protease inhibitors are triterpenoids, particularly boswellic acid, betulinol, and betulinic acid, or extracts containing same in substantial quantities.

It will be recognized from the foregoing that either an extract or the individual protease inhibitor can be used, and that the individual protease inhibitors can also be found in other types of extracts. The amount of active material used will vary depending upon the whether an extract or isolated compound is used, the concentration of active material in a given extract, and the known potency of the active material. However, the concentration of active protease inhibitor in the final product should generally be between about 0.001 to about 10%, preferably about 0.05 to about 5%, more preferably about 0.1 to about 1%, by weight of the total composition.

The second component is a cellular differentiation enhancer. Such compounds act in the present invention to increase the ability of the relevant epidermal cells to synthesize the lipids that constitute the primary component of the barrier. The epidermal cells that produce lipids do not do so during their entire life cycle, however, but do so only at the point of differentiation. If this differentiation is delayed to the point, at which the epidermal cells reach their terminal point in migration, to the skin surface, the production of lipids is concurrently delayed, and therefore, their effect, if any, is diminished. The differentiation enhancers used in the invention stimulate the earlier production of lipids from epidermal cells, thereby increasing the length of time, over which the lipids are being produced, and presumably concurrently increasing the lipid content of the barrier. Several types of cellular differentiation inhibitors, are known, and these include, but are not limited to sclareolide, forskolin, 7-dehydrocholesterol, and Vitamin D3analogs. The differentiation enhancer also will be used in amount consistent with its known activity, 0.001 to 10%, preferably about 0.0025 to about 5%, more preferably about 0.05 to about 1%, by weight of the total composition.

The combination of the protease inhibitor and the differentiation enhancer is shown to have a strong effect on barrier repair when compared with control vehicles and with other compounds commonly used in skin enhancement. Specifically, on skin that had been challenged with tape stripping, it was found that combination of these two components exhibits about a 50% increase in barrier repair, as measurable by transepidermal water loss, in comparison with the placebo, after a period of three days. Thus, this combination on its own is shown to be able to increase barrier function substantially.

Although the noted combination is highly effective on its own, it has been further shown that the combination achieves even further enhancement of barrier function by its combination with, certain other skin enhancement compounds. More specifically, the combination with one or more of certain specific skin enhancers. In a preferred embodiment, the barrier repair combination is further combined with cholesterol sulfate, which in the present specification and claims is intended to refer to the corresponding plant-derived material, phytosterol sulfate. Cholesterol sulfate, as described in Applicants' copending application Ser. No. 09/246,607, incorporated herein by reference, also has an effect on the skin, by increasing the cohesion of the stratum corneum. Thus, its combination with the protease inhibitor/differentiation enhancer even further strengthens the ability of the composition maintain the integrity of the stratum corneum. The amount of cholesterol sulfate employed is preferably about 0.05 to about 10%, preferably from about 0.5 to about 5%, most preferably about 1 to about 3%, by weight of the total composition.

In all formulations in which cholesterol sulfate is employed, and in a particularly preferred embodiment, it is preferred that the composition also contain other components of the naturally occurring lipid barrier. In a particularly preferred embodiment, the cholesterol sulfate is combined with at least, one of each of fatty acids, ceramides, and a sterol, preferably cholesterol or phytosterol. Fatty acids may be up to 24 carbon atoms in length. Examples of preferred fatty acids include butyric acid, caproic acid, octanoic acid, decanoic acid, dodecanoic acid, tetradecanoic acid, palmitic acid, stearic acid, linoleic acid and oleic acid. Particularly preferred are fatty acids with a $C_{12}$ to $C_{20}$ chain length.

The ceramides to be employed in the compositions of the invention are sphingolipids, having a sphingesine or related molecule backbone with fatty acids or .omega.-esterified fatty acids linked to an amino group on the sphingosine, and in some cases, with saccharide moieties linked to the terminal hydroxyl of the sphingesine. In particular, the compositions may contain .omega.-esterified ceramides or acylceramides, cereforosides, .omega.-esterified cerebrosides, or acylglycosyl sphingolipids. Particularly preferred types of ceramides for the present compositions are ceramide III and cerehrosides.

In those compositions in which cholesterol sulfate is combined with these lipids, the lipid components each can be used in an amount of from about 0.05 to 10%, preferably 0.5 to about 5%, most preferably about 1 to about 3%, all by weight of the total composition. In a particularly preferred embodiment, the cholesterol sulfate and the lipid components are present in substantially equal amounts in the composition. It will be understood from the foregoing that the lipid component need not be pure lipid, but rather may be natural extracts containing one or more desirable lipids, and used in amounts consistent with attaining the concentrations recommended above.

The effect of the present compositions in effecting barrier repair or maintaining the integrity of the skin's outer layer can be applied to a number of different uses. For example, the compositions can be used to treat any condition in which a deficient or faulty barrier is a factor. In this regard, the compositions can foe used to improve the long term moisture retention of the skin, or in prevention or treatment of dry skin conditions generally, or specific dry skin conditions, such as result from regular exposure to detergents, soaps and hot water; seasonal exposure to harsh weather conditions, e.g., cold, wind and/or sun; occupational exposure to harsh chemicals or other drying or damaging agents; or pathological conditions such as eczematous dermatides, psoriasis, ichthyoses, xerosis and the like. It is also well-known that dry skin is commonly associated with aging (both intrinsic and photoaging), and the compositions can be used in prevention of further damage to aging skin, or treatment and/or reversal of already present damage, including the appearance of fine lines and wrinkles, which, are frequently associated with dry skin and the thinning of the stratum corneum that occurs with age. The compositions can also be used in the treatment of a defective skin barrier, such, as occurs on the soles of the feet, and palms of the hands, where the stratum corneum is very thick, but the lipid barrier is poor. In addition, defective skin barriers frequently occur in association with burns, wounds, blisters, stasis ulcers and bedsores; such injuries can be expected to benefit from application of the compositions.

In further use of the compositions of the invention is in reduction of the skin's response to irritants and sensitizers. A significant percentage of the population considers itself to have sensitive skin, in that they perceive a frequent, stinging or painful response to various elements to which the skin may be exposed, be it through makeup or skin care products, environmental stimuli such as smoke or pollution, or occupational exposure to chemicals. In addition, even normal skin can have a reaction to exposure to known irritants, such as acids. As it is well known that the stratum corneum and lipids constitute the first line of defense against irritants, by providing a physical barrier to permeability of such materials to the lower skin layers, the application of the compositions of the invention, by increasing the integrity of the barrier, can reduce the reactivity of the skin of both normal and sensitive individuals to irritants and sensitizers, in one embodiment, for example, the compositions can be used to reduce the reaction of the skin to the irritation caused by therapeutic acids such as alpha and beta hydroxy acids, retinoic acid, and the like, or to reduce the irritation caused by insect bites or stings, or alleviate the irritation experienced with contact dermatitis.

The increased cohesion of the stratum corneum brought about by the compositions of the invention also provides other benefits. The stratum corneum represents an important physical barrier between the environment and the deeper skin layers as well as the internal organs. The presence of this thicker layer thus will provide a greater level of protection than is possible with weaker barrier. Perhaps the most important aspect of this effect is the enhanced self-protection from UV rays. The thicker stratum corneum means an increase in the Minimal Erythemal Dose of UV which will result in sunburn or more serious skin damage. In connection with this aspect of the invention, the components of the invention may foe beneficially combined with one or more sunscreens for an enhanced UV protective composition which provides both short- and long-term protection. Thus, the invention provides sunscreen compositions comprising effective amounts of the components of the composition of the invention, and one or more sunscreens. Examples of useful sunscreens include, but are not limited to, inorganic sunscreens such as titanium dioxide, sine oxide, and iron oxide; and organic sunscreens, such as camphor derivatives, cinnamates, salicylates, benaophenones, triazines, PABA derivatives, diphenylacrylate derivatives, and dibenzoylmethane derivatives. In such sunscreen compositions, the components of the invention are present in the amounts described above, and the respective sunscreens are present in the amounts normally used for UV protection.

An additional use of the compositions of the invention is in the enhancement and prolongation of self-tanning products. One of the recognised limitations of self-tanners, which are normally based on dihydroxyacetone (DHA) as the active component, is that the tan on the skin lasts only as long as the skin cells receiving the DHA remain in place. In the normal course of events, then, a self-applied tan usually lasts no more than 5 days, i.e., for as long as it takes for the stratum corneum layer to which the DHA was applied to fully turn over. When the compositions of the invention are combined with DHA, or any other self-tanning agent, in a typical self-tanning formulation, however, the rate of turnover of the stratum corneum to which the composition is applied is slowed down, thereby permitting a longer rate of retention of the "tanned" cells, and thus prolonging the length of time the tan remains visible on the skin. Thus, the invention provides a self-tanning composition comprising a protease inhibitor, a cell-differentiation enhancer, and an effective amount of a self-tanning agent, optionally containing cholesterol sulfate and the lipid component. In a preferred embodiment, the self-tanner is DHA, which is usually applied in an amount of from about 2.5 to about 10% by weight of the formulation. The self-tanner may also be imidazole, preferably in combination with. DHA, in an amount of about 1-10%, preferably about 1.5-7.5%.

The compositions of the invention are employed in a manner appropriate to the intended final use of the product. For example, in the treatment of occasional dry skin due to exposure to weather or other temporary conditions, or in the treatment of occasional skin irritation, the compositions can be used on an as-needed basis until the condition is relieved. When being used to treat a more permanent condition, for example, a condition associated with a defective or deficient lipid barrier, particularly sensitive skin, dry skin associated with any type of aging, or the wrinkling or fine lines associated with a thinning of the stratum corneum with aging, the composition, is preferably applied chronically, to prevent recurrence of the condition. For this purpose, it is suggested as an example that topical application of the composition, in an amount of from about 0.1 mg/cm$^2$ to 2 mg/cm$^2$ of skin, be performed, from about once per week to about 4 or 5 times daily, preferably from about 3 times a week to about 3 times daily, most preferably about once or twice per day. By "chronic" application, it is meant, herein that the period of topical application may be over the lifetime of the user, preferably for a period of at least about one month, more preferably from about three months to about twenty years, more preferably from about six months to about ten years, more preferably still from about one year to about five years, thereby resulting in the treatment or prevention of the condition in question.

When the composition is used in conjunction with a sunscreen, it is applied in the same amounts as specified above, on an as-needed basis, to mitigate the effects of exposure to the sun. When used in combination with a self-tanner, the composition is also applied in similar amounts, on the portion of the skin to be tanned, with repetition, again, on an as-needed basis.

The invention is further illustrated by the following non-limiting examples:

EXAMPLES

Example 1

A study is conducted to determine the efficacy of certain compositions in enhancing repair of the lipid barrier. Female volunteers with normal skin, who are in good general health, free of any dermatological disorders, participate in the study. Their skin barrier is challenged by tape stripping according to the procedure outlined below. After their evaluation, the subjects receive a treatment every day on the right side of their face. They are also given the product containing the actives to use once every night for three nights, on the right side of the face only, the left side being the untreated control side. A separate group is given a placebo, without actives, as treatment product.

To challenge the barrier, the subjects are acclimated in an environmental room at 40% relative humidity and 70° C. for 15-20 minutes. A 5 cm by 1 cm area is marked on the lower right cheek near the jaw line and initial water evaporation measurements are taken in three separate spots approximately 1 cm apart in a row. Five cm of cello-tape is placed on the skin in the outlined area, starting from the top of the cheek and after one firm stroke in each direction it is removed by gently pulling in a downward direction parallel to the skin. The procedure is repeated and water evaporation is measured after every five strips until the barrier is disrupted as indicated by a minimum of 18 g/sq.m hr on one of the three spots. Both sides of the face are stripped in the same way. The subjects returned for TEWL evaluation 1, 2 and 3 days after tape stripping of the skin to monitor the repair, Barrier repair is evaluated by first challenging the skin as described above. One side is product-treated 2 times a day, and the other is the untreated control. Repair is measured in the increase in the recovery of the skin on the stripped and treated site compared to the stripped untreated site. From this, total repair is calculated over three days by calculating the change in the area parameter, The smaller the area, the taster the repair.

Treatment products are (1) a composition containing 0.1% sclareolide and 0.2% white birch extract; (2) a composition containing 0.1% sclareolide and 0.2% boswellic acid; (3) a composition containing 0.2% each of phytocohesine (phytosterol sulfate), ceramides (wheat-derived ceramides), boswellic acid, cholesterol, and linoleic acid, and 0.1% sclareolide. The results obtained indicate for composition (1), barrier repair is 50% over placebo; for composition (2), repair is 59% over placebo, and composition (3) is shows barrier repair at 78% over the placebo, each composition therefore showing substantial efficacy in barrier repair.

What we claim is:

1. A method for improving skin lipid barrier function comprising applying to the skin a composition comprising from 0.001 to 10% of at least one protease inhibitor which is *Boswellia* extract, and from 0.001 to 10% of at least one cell differentiation enhancer which is forskolin the composition further comprising about 0.05 to 10% of each of cholesterol, a fatty acid, a ceramide, and a sterol.

2. The method of claim 1 wherein the *Boswellia* extract and the forskolin stimulate the repair of a damaged lipid barrier.

3. The method of claim 1 wherein the composition is applied from 1-2 times per day.

4. The method of claim 1 wherein the composition is applied to skin from 1-2 times per day for 1-3 months.

5. The method of claim 1 wherein the fatty acid is a C12-C20 fatty acid.

6. The method of claim 1 wherein the composition further comprises at least one sunscreen.

7. The method of claim 1 wherein the composition further comprises a self tanning agent.

8. The method of claim 7 wherein the self tanning agent is dihydroxyacetone.

9. The method of claim 1 wherein the cholesterol is cholesterol sulfate.

10. The method of claim 1 wherein the skin to which the composition is applied is dry skin.

11. The method of claim 1 wherein the skin to which the composition is applied is irritated or sensitized skin.

12. The method of claim 1 wherein the skin to which the composition is applied is exposed to UV radiation.

13. The method of claim 1 wherein the ceramide is ceramide III.

\* \* \* \* \*